United States Patent [19]

Yasis et al.

[11] Patent Number: 5,702,753

[45] Date of Patent: Dec. 30, 1997

[54] METHOD OF MANUFACTURING A DIAGNOSTIC ELECTRODE

[75] Inventors: Rafael M. Yasis, White Bear Lake; Rosa Uy, St. Paul; Barbara J. Marcus, Cottage Grove; Steven S. Kantner, St. Paul, all of Minn.

[73] Assignee: Minnesota Mining And Manufacturing Company, St. Paul, Minn.

[21] Appl. No.: 343,253

[22] Filed: Nov. 22, 1994

[51] Int. Cl.⁶ .................. B05D 3/00; A61B 5/0408
[52] U.S. Cl. .......................... 427/2.12; 128/640
[58] Field of Search .................. 128/639, 640, 128/641, 642; 607/148, 149, 152; 427/2.12

[56] References Cited

U.S. PATENT DOCUMENTS

| 3,972,329 | 8/1976 | Kaufman . | |
|---|---|---|---|
| 4,304,235 | 12/1981 | Kaufman | 607/152 |
| 4,643,193 | 2/1987 | De Marzo | 128/639 |
| 4,852,571 | 8/1989 | Gadsby et al. | 128/640 |
| 4,934,383 | 6/1990 | Glumac | 607/152 |
| 5,080,099 | 1/1992 | Way et al. | 128/640 |
| 5,276,079 | 1/1994 | Duan et al. | 128/640 |
| 5,496,363 | 3/1996 | Burgio et al. | 128/640 |

*Primary Examiner*—Lee S. Cohen
*Attorney, Agent, or Firm*—John H. Hornickel; Gary L. Griswold; Walter N. Kirn

[57] ABSTRACT

A method of making and using diagnostic electrodes is disclosed. The method of making involves the coating of both conductive adhesive and biocompatible pressure sensitive adhesive on to a flexible non-conductive backing material on a side that has at least a portion thereof covered with an electrically conductive surface. The method of coating the electrodes is very cost efficient and economical. The use of the electrode enjoys the advantage of controlled coating thicknesses such that both types of adhesive in their final thicknesses have contact with skin of a patient.

9 Claims, 2 Drawing Sheets

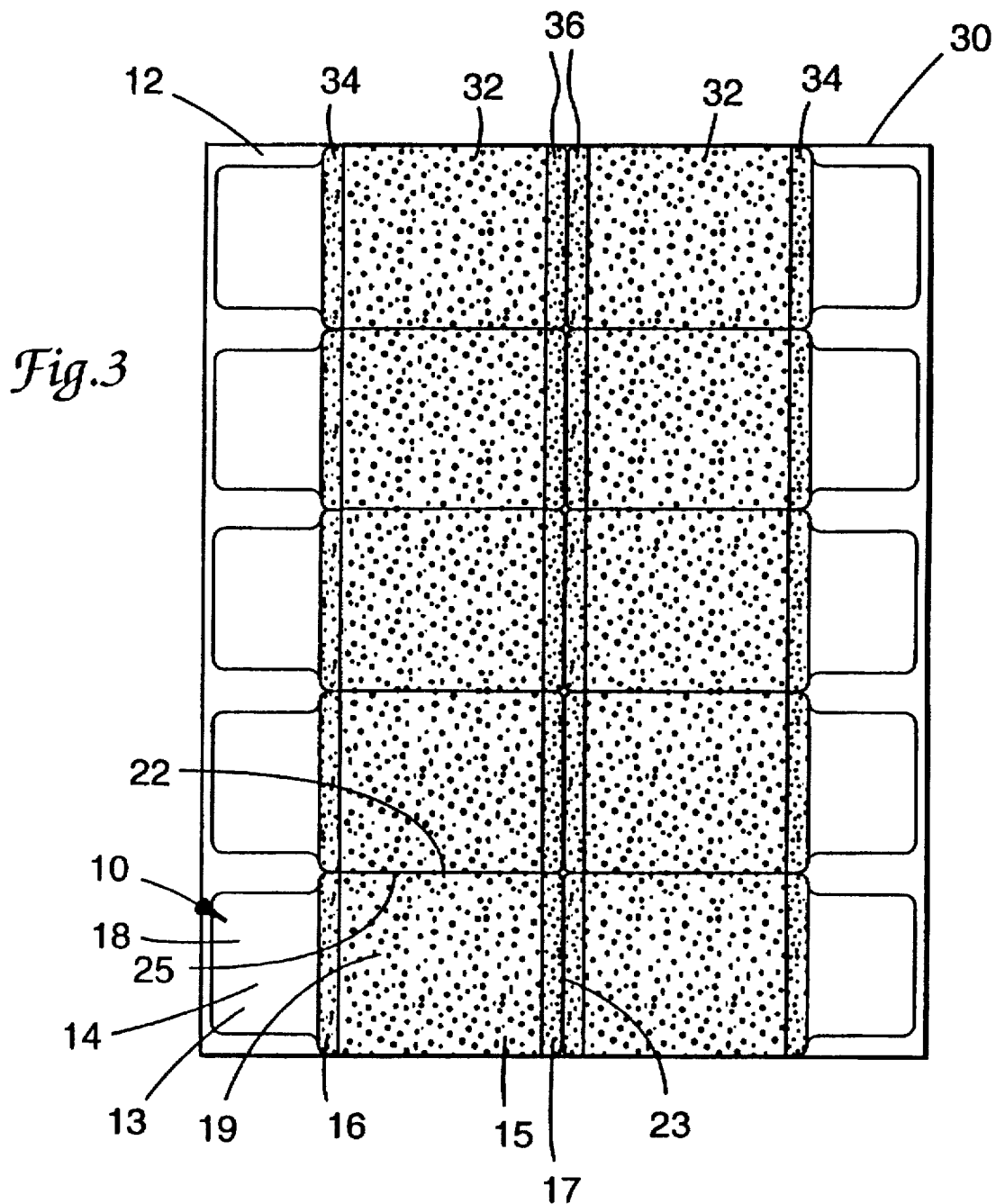

5,702,753

METHOD OF MANUFACTURING A DIAGNOSTIC ELECTRODE

FIELD OF THE INVENTION

This invention relates to the making and using of diagnostic biomedical electrodes.

BACKGROUND OF THE INVENTION

Diagnostic biomedical electrodes are used for the diagnosis of medical conditions by receiving faint electrical signals emanating from the body of a patient. "Diagnostic electrode" includes electrodes for both the diagnosis of abnormal medical conditions and the monitoring of changes in medical conditions. Electrocardiography is especially reliant on the use of diagnostic biomedical electrodes to receive and transmit electrical signals from the various movements of heart muscles and valves to electrical instrumentation where heart conditions can be diagnosed.

The contact of biomedical electrodes with mammalian skin of a patient requires the ability to detect the faint electrical signals. In the last several years, a variety of structures of biomedical electrodes have been designed and used. In each instance, the electrode has employed a field of conductive adhesive to adhere to mammalian skin and to receive the electrical signals and transmit them ionically to an electrically conductive surface for electrical connection to the electrical diagnostic instrumentation.

Representative examples of biomedical electrodes that have been used for, or described as useful for, diagnostic purposes include U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); and 5,296,079 (Duan et al.).

Because of the number of diagnostic electrodes required for each electrocardiogram (ECG) procedure, usually about 10, and because of the single use of such electrodes usually provided, the cost of such electrodes to customers makes diagnostic electrodes very sensitive to manufacturing techniques and performance features. Unfortunately in some diagnostic electrodes, the cost of manufacture outweighs the performance properties of the electrode. For example, some biomedical electrodes rely exclusively on the adhesiveness of the field of ionically conductive adhesive to maintain proper contact with mammalian skin, while others provide an expensive surround or border of biocompatible pressure sensitive skin adhesive about the field of conductive adhesive. One such construction is disclosed in U.S. Pat. No. 4,798,208 (Faasse, Jr.). In the present competitive environment, the latter usage of a second type of adhesive is too costly while the former usage of no skin adhesive can be inadequate for assured adhesion for diagnostic purposes.

SUMMARY OF THE INVENTION

The present invention solves a problem found in the prior art biomedical electrodes by providing an extremely efficiently manufactured diagnostic electrode that meets manufacturing cost requirements for the current competitive environment while also providing a second type of adhesive for assured adhesion of the electrode during the ECG procedure.

The present invention comprises a method of using a diagnostic electrode, comprising: (a) providing an electrode for diagnosis or monitoring of electrical signals in a mammal, wherein the electrode comprises a non-conductive flexible backing having an electrically conductive surface contacting both a field of coated conductive adhesive and two opposing fields of coated biocompatible pressure sensitive skin adhesive; and (b) contacting the electrode to mammalian skin and to electrical instrumentation to perform an electrocardiographic procedure.

The present invention also comprises a method of making an electrode, comprising: (a) providing a non-conductive flexible backing having a side having an electrically conductive surface; (b) coating at least one field of biocompatible pressure sensitive adhesive on the side; and (c) coating a field of conductive adhesive on the electrically conductive surface.

A feature of the invention is the electrode combines the required elements of an electrode having excellent trace quality, a reproducibility property of biomedical electrodes during usage, with the desirable elements of excellent mammalian skin adhesion.

Another feature of the invention is that the two types of adhesive, ionically conductive adhesive and biocompatible pressure sensitive skin adhesive, have similar thicknesses to permit excellent adhesion of both types of adhesive with mammalian skin for different but mutually required purposes.

An advantage of the invention is the application of efficient manufacturing methods to produce a superior electrode that can be used in the diagnosis of patients during ECG procedures.

Another advantage of the present invention is the method of coating two types of pressure sensitive adhesive on to a single substrate material can control the thicknesses of the adhesives in order to provide a match of final thicknesses desirable for a consistent contact of the electrode to skin of a patient during ECG and other biomedical procedures. Use of a combination of tapes of adhesives and coatings of adhesives as done in prior art electrodes is a more complicated manufacturing procedure involving different types of assembly equipment and can require more detailed processing to provide multiple layers of a tape for one type of adhesive adjoining a coated field of another type of adhesive. Thus, the present invention provides a significant manufacturing advantage and a significant usage advantage over prior art electrodes that rely on two types of assembly of adhesives for two types of adhesives.

Embodiments of the invention are described in greater detail with reference to the following drawings.

BRIEF DESCRIPTION OF THE DRAWING

FIG. 3 is an array of diagnostic electrodes during manufacture.

EMBODIMENTS OF THE INVENTION

Figure 1:
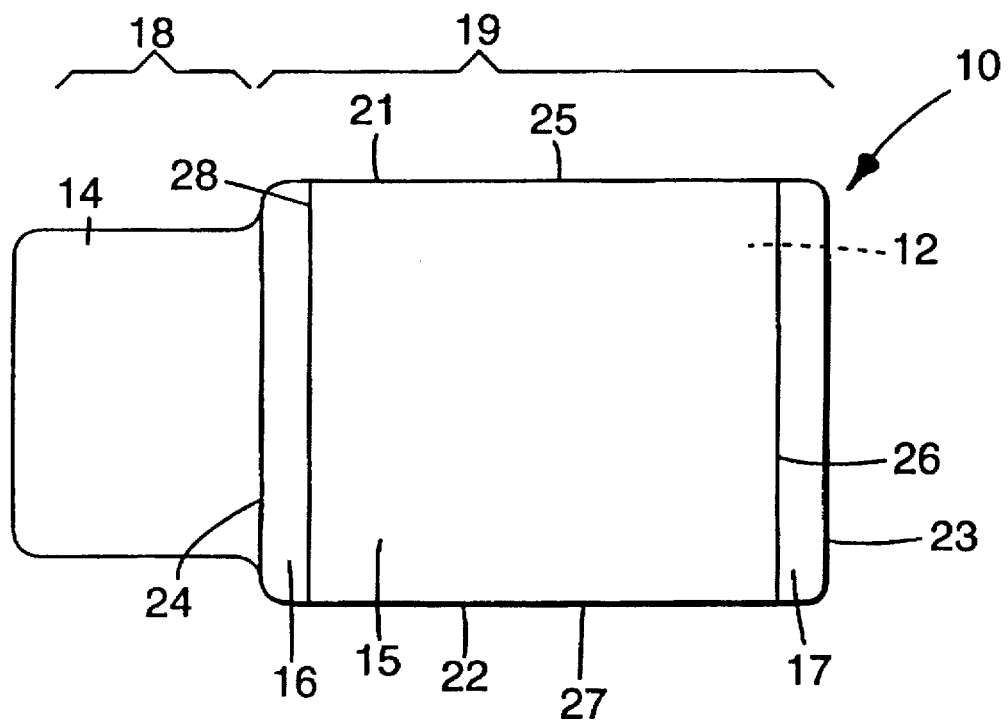
FIG. 1 is a bottom plan view of a diagnostic electrode according to the present invention.
Figure 2:
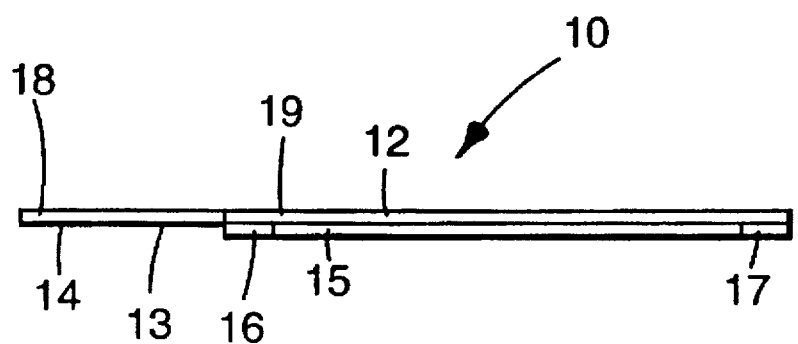
FIG. 2 is a side plan view of the diagnostic electrode of FIG. 1.

FIGS. 1 and 2 are bottom and side plan views, respectively, of one embodiment of a diagnostic electrode 10 of the present invention. From the surface farthest away from mammalian skin, electrode 10 comprises a non-conductive flexible backing 12 having a side 13 having on at least a portion thereof an electrically conductive surface 14 contacting a field 15 of conductive adhesive. Two separate opposing fields 16 and 17 of biocompatible pressure sensitive skin adhesive contact side 13 and preferably electrically surface 14. Not shown is a release liner that contacts fields 15, 16, and 17 of adhesive when electrode 10 is not in use.

Flexible backing 12 comprises a tab portion 18 and a pad portion 19. Both tab portion 18 and pad portion 19 have electrically conductive surface 14, but field 15 of conductive adhesive contacts only pad portion 19. Tab portion 18 is suitable for releasable attachment to a electrical connector that delivers the ECG signals to the electrical instrumentation.

Pad portion 19 has a perimeter defined by edges 21, 22, 23, and 24. By comparison, field 15 of conductive adhesive has a perimeter defined by edges 25, 26, 27, and 28. The surface area of field 15 of conductive adhesive within edges 25–28 contacts the surface area of pad portion 19 within edges 21–24 of pad portion 19.

Fields 16 and 17 of biocompatible skin adhesive are not ionically conductive as is field 15 but are preferably contacting pad portion 19 in separate locations on side 13 and preferably in separate locations on electrically conductive surface 14 to assist in the maintenance of adhesive contact of electrode 10 to skin of a mammalian patient. The separate opposing locations on pad portion 19 proximal and distal to tab portion 18 provide a relatively high level of adhesion to mammalian skin because the electrode 10 has added adhesiveness in the two locations most likely to be affected by edge lifting of the electrode 10 due to stress applied to the electrode 10 during use: along a line bisecting both the tab portion 18 and the pad portion 19. Added adhesiveness to surround pad portion 19, i.e., providing pressure sensitive adhesive also contacting pad portion 19 at edges 21 and 22, such as disclosed in U.S. Pat. No. 4,798,208, is unnecessary according to the present invention and involves additional manufacturing cost without suitable performance benefit.

In several mammalian species certain types of skin have a high concentration of oil secreting glands that can disrupt continued adhesion of electrode 10. Since during ECG and other medical procedures, it is critical to maintain continuous adhesive contact, assurance of adhesion of electrode 10 to the skin throughout the procedure is important. The present invention has found that a field 16 at a location proximal to tab portion 18 (contacting pad portion 19 at edge 24) and a field 17 at a location distal to tab portion 18 (contacting pad portion at edge 23) provides significant resistance to lifting compared with electrodes that do not have such additional adhesive fields 16 and 17. Yet because of the method of coating such fields 16 and 17 according to the present invention, and confining the location of such fields to be bisected by a line also bisecting the tab portion 18 and pad portion 19, the present invention provides both manufacturing and performance advantages unknown in the art.

As will be apparent to one skilled in the art, when a patterned electrically conductive surface is used, such as disclosed in International Patent Publications WO 91/05509 and WO 93/00857, the field(s) of nonconductive biocompatible pressure sensitive adhesive need not contact the patterned electrically conductive surface 14. Rather, the field 16 or field 17, or both, can contact side 13 that does not have the electrically conductive surface 14.

As seen in FIG. 2, a feature of the present invention is the direct contact of biocompatible pressure sensitive skin adhesive fields 16 and 17 to side 13, and preferably electrically conductive surface 14, of pad portion 19.

Another feature of the present invention is that the final thickness (after processing) of fields 16 and 17, ranging from about 0.25 mm to about 0.75 mm thick, and preferably about 0.50 mm thick, is within 40 percent, and preferably within 20 percent, of the final thickness of the field 15 of ionically conductive adhesive. Ideally, the final thickness of field 15 and fields 16 and 17 are equal or within a difference of less than 10 percent. Significantly, thickness of fields 16 and 17 being within 20 percent of the thickness of field 15 permits electrode 10 to have an extremely low and consistent profile for adhesion of electrode 10 to skin of a patient. Both the conductive adhesive field 15 and the biocompatible pressure sensitive adhesive fields 16 and 17 have adequate contact with skin of the patient because neither type of adhesive is disadvantaged in distance from contact with the skin due to the thickness of the other adhesive. It is an advantage of the present invention that the method of making the electrode can achieve such low and consistent profile of adhesives on the electrode in a cost-effective manner. Only the application of both types of adhesive according to the method of the present invention can account for cost-effective, excellent performing diagnostic electrodes useful according to the present invention.

Selection of materials to construct electrode 10 are known to those skilled in the art of biomedical electrode construction. U.S. Pat. Nos. 4,352,359 (Larimore); 4,524,087 (Engel); 4,539,996 (Engel); 4,554,924 (Engel); 4,848,348 (Engel); 4,848,353 (Engel); 5,012,810 (Strand et al.); 5,133,356 (Bryan et al.); 5,215,087 (Anderson et al.); 5,296,079 (Duan et al.); and U.S. Pat. No. 5,385,679 (Uy et al.) all describe suitable materials for the construction of biomedical electrodes useful for ECG procedures, and all are incorporated by reference as if fully rewritten herein.

Of the numerous electrically nonconductive materials known to those skilled in the art, presently preferred for backing material 12 are polyester films of about 0.1 mm thickness commercially available as "Melinex" branded films (e.g., 329 and 339) from ICI Americas of Hopewell, Va. Preferably, the film can be treated with a corona treatment to improve the adhesion of the electrically conductive surface to the backing material.

Of the numerous electrically conductive materials known to those skilled in the art, inks containing electrical conductive particles such as graphite or metals are useful with metal-containing inks being preferred. Presently preferred for electrically conductive surface 14 is a silver containing ink such as "N-30" ink, a silver/silver chloride containing ink such as "R-300" ink, or R-301MPK (+240)® ink, all commercially available from Ercon, Inc. of Waltham, Mass.

Of the numerous conductive adhesives known to those skilled in the art, field 15 of conductive adhesive can be those conductive adhesives as described in the table at Column 16 of U.S. Pat. No. 5,012,810 (Strand et al.) and as disclosed in U.S. Pat. Nos. 4,524,087; 4,539,996; 4,848,353; and 4,554,924 (all Engel); 5,296 079 (Duan et al.); U.S. Pat. No. 5,385,679 (Uy et al.); and U.S. Pat. No. 5,338,490 (Dietz et al.) all of which are incorporated by reference herein. Presently preferred for field 15 of conductive adhesive is a poly(N-vinyl pyrrolidone) radiation crosslinked and plasticized with glycerol prepared according to the disclosure of U.S. Pat. No. 5,296,079 (Duan et al.), which is incorporated by reference herein.

Of the numerous biocompatible skin adhesives known to those skilled in the art, presently preferred for fields 16 and 17 of adhesive are acrylate pressure sensitive adhesives and tackified polystyrene-polyisoprene block copolymers pressure sensitive adhesives. Such acrylate ester copolymer adhesives are generally described in U.S. Pat. Nos. 2,973,286; Re 24,906; Re 33,353; 3,389,827; 4,112,213; 4,310,509; 4,323,557; 4,732,808; 4,917,928; 4,917,929; and European Patent Publication 0 051 935, all incorporated herein by reference. Tackified block copolymer adhesives are generally described in Ewins, "Thermoplastic Rubbers: A-B-A Block Copolymers" which is Chapter 13 of Satas, Ed., *Handbook of Pressure Sensitive Adhesive Technology*, Second Edition, Van Nostrand Reinhold, 1989, which is incorporated herein by reference. Use of tackified block copolymer adhesives as biocompatible skin adhesives in biomedical electrodes is described in U.S. Pat. No. 4,204,312.

A variety of coating methods is available for both the conductive adhesive and the biocompatible skin adhesive including extrusion coating, knife coating, and curtain coating as described in Satas, "Coating Equipment" which is Chapter 34 of Satas, Ed., *Handbook of Pressure Sensitive Adhesive Technology*, Second Edition, Van Nostrand Reinhold, 1989, which is incorporated herein by reference. Hand knife coating can be employed. A slot die is preferably used, which can include an extrusion die, a knife die, a curtain coating die and other types of slot dies with a high shear flat wiping lip, a medium shear flat wiping lip, a medium shear rod wiping lip, or a sharp knife wiping lip, which are generally described in Lippert, "Slot Die Coating for Low Viscosity Fluids", which is Chapter 11 of Satas, Ed., *Coatings Technology Handbook*, Marcel Dekker, Inc., 1991, which is incorporated by reference herein. The choice of the coating method and use of slot dies depend on the nature of the adhesive precursor, whether it is a high viscosity 100% solids hot-melt, a moderate viscosity 100% solids material to be polymerized on-web, or a moderate to low viscosity solvent or water delivered material. One skilled in the art will recognize that in the latter case, the coating step includes a drying process and this drying process results in a final thickness of adhesive that is thinner than the thickness at the coating head due to loss of solvent or water. The final thickness of conductive adhesive should be within 40% of the final thickness of the biocompatible pressure sensitive adhesive in order for both types of adhesive to have contact with the skin of a patient.

METHOD OF PREPARING DIAGNOSTIC ELECTRODES

To perform a cost effective manufacture of electrodes 10 from a single sheet 30, constructed from backing material 12 having electrically conductive surface 14, sheet 30 is configured in a manner to be cut into an array of electrodes 10 having tab portions 18 and pad portions 19 as shown in FIG.3. Edges on each pad portion 19 distal to tab portion 18 are aligned and contiguous. This array provides electrodes aligned back edge to back edge. Preferably, an array of 10 diagnostic electrodes 10 can be arranged for coating of adhesives according to the present invention.

The combination of fields of adhesive 15, 16, and 17 can be coated from dies as stripes 32, 34, and 36, respectively, of contiguous coatings to provide on each pad portion 19 a field 16 of skin adhesive contacting electrically conductive surface 14 in a location proximal to tab portion 18, a field 15 of ionically conductive adhesive contacting electrically conductive surface 14 in a central area of pad portion 19, and a field 17 of skin adhesive contacting electrically conductive surface 14 in a location distal to tab portion 18. The coating width of skin adhesive stripe 36 for field 17 is twice the coating width of skin adhesive stripe 34 for field 16, in order to permit single coating stripe 36 to provide fields 17 for contiguous pad portions 17 at the edge distal to their respective tab portions 18.

The coatings 32, 34, and 36 can be applied to result in a thickness ranging from about 0.25 mm to about 0.75 mm and preferably about 0.50 mm thick. Preferably, the final thickness of field 15 is not more than about 20 percent different than the final thickness of fields 16 and 17.

Having coated stripes 32, 34, and 36 across each contiguous pad portion 19, the array of electrodes 10 can be formed by cutting between adjoining edges 25 and 22 and between adjoining edges 23.

As seen in FIGS. 1 and 3, coated adhesive fields 15, 16, and 17 are arrayed on electrically conductive surface 14 to provide a cost efficient method of manufacture of electrodes 10 which have superior adhesive performance properties against mammalian skin because of fields 16 and 17 of biocompatible pressure sensitive skin adhesive provide excellent adhesion while field 15 of conductive adhesive of similar final thickness to fields 16 and 17 receives electrical signals for the ECG procedures. As such the present invention provides a superior method of using diagnostic electrodes for ECG procedures.

An alternative embodiment to electrode 10 can be constructed by providing only a single field 16 of biocompatible pressure sensitive skin adhesive adjoining field 15 of conductive adhesive and contacting electrically conductive surface 14 on pad portion 19. In this embodiment, field 17 of adhesive distal to tab portion is not utilized. However, the percentage differential final thickness between field 16 and field 15 are not significantly different than in the first embodiment as seen in FIGS. 1 and 2.

Further explanation of embodiments of the invention are provided in the following examples.

EXAMPLE 1

Part A—Stripe Coating a Tackified Kraton Adhesive Using a Hot Melt Method

A 30.5 cm slot die having lips curved to the radius of a 11.4 cm diameter aluminum backup roll was fitted with a 0.76 mm thick shim insert which was patterned with openings consisting of three pairs of stripes. Each pair was spaced 3.2 cm apart with 3.8 cm between the pairs. Each stripe was 0.64 cm wide. A Graco/LTI Dynamelt DM-5 pail unloader with heated platen and hose (both 175° C.) was used to pump adhesive from a 19 liter pail to the die, also held at 175° C. The adhesive formulation was a mixture of 25 weight percent Kraton 1112® (a polystyrene-polyisoprene block copolymer available from Shell Chemical Co., Houston, Tex.), 55 weight percent Wingtack Plus® (a modified polyterpene tackifying resin available from Goodyear Tire and Rubber Co., Akron, Ohio), and 20 weight percent Tufflo 6056® (a white mineral oil available from Lyondell Lubricants, Houston Tex.). These materials had been compounded together using a twin screw extruder and the resulting molten mixture placed in pails. The slot fed die was positioned against an 11.4 cm diameter aluminum backup roll and a 30.5 cm wide web of 75 µm clear polyester film (Melinex® 505 available from ICI Films, Hopewell, Va.) covered with a gravure coating of R-301MPK (+240)® conductive silver/silver chloride ink (available from Ercon Incorp., Waltham, Mass.) was unwound past the die at 6 meters per minute. With a setting of 120 on the pail unloader, 0.64 cm wide stripes with a final thickness of 0.43 mm were obtained at this line speed. Higher pump speeds or smaller nip gaps gave a smoother stripe as the lip of the die spread the adhesive, but this tended to widen the stripe to 0.95 cm or more. The resulting stripe coated film was wound up with an Akrosil® 64 µm siliconized polyethylene release liner (available from Akrosil, Menasha, Wis.) laminated against the adhesive coated side.

EXAMPLE 1

Part B—Coating Ionically Conductive Adhesive Between Paired Stripes of Hot Melt PSA The silver/silver chloride ink coated polyester film coated in Example 1, Part A above in a pattern of three pairs of 0.64 cm wide 0.43 mm thick tackified Kraton PSA stripes, each pair spaced 3.2 cm apart with 3.8 cm between the pairs was further coated with an ionically conductive adhesive precursor using an unheated slot die having lips curved to the radius of a 11.4 cm diameter aluminum backup roll. The die had a 1.27 mm thick shim insert which was patterned with three 3.2 cm openings positioned 5.1 cm apart to allow for stripe coating of the conductive adhesive precursor between the paired stripes of Kraton PSA. The conductive adhesive precursor had a formulation of 10.7 weight percent micronized poly(N-vinyl pyrrolidone) (available from ISP, Wayne, N.J.) which had been lightly crosslinked by exposure to gamma irradiation, 22.0 weight percent glycerin (available from Dow Chemical, Midland, Mich.), 0.7 weight percent potassium chloride (available from J. T. Baker, Philipsburg, N.J.), and 66.7 weight percent deionized water. The use of such formulations for ionically conductive adhesives is described in U.S. Pat. No. 5,296,079 (Duan et al.). This precursor was coated onto the substrate by passing through a stator/rotor type homogenizer at 4000 rpm to reduce viscosity and pumping to the slot die with a 10 cm$^3$ Zenith gear pump. The polyester substrate was unwound at 1.4 meters per minute, the top Akrosil liner stripped, the precursor coated at 0.89 mm thick and dried in a 6 meter long chamber using infra red heating. The energy supplied to the infra red elements was such that the temperature of an uncoated web is raised to 120° C. at these line speeds. A second Akrosil liner was laminated to the now dried web, which was then wound up. The dried conductive adhesive had a final thickness of 0.38 mm and a water content of 20 weight percent. Under these conditions the stripes of this Kraton adhesive tended to soften and flow.

EXAMPLE 1

Part C—Converting to Electrodes and Testing

Using a steel rule die, electrodes were cut out of this liner/adhesive/backing laminate leaving an uncoated 1.6 cm wide by 1.0 cm long rectangular tab centered along the Kraton stripe side of a 2.2 cm by 2.2 cm square body. The resulting electrodes were used in a study assessing lift scores in a resting EKG panel. Each of 12 panelists had samples of the electrode placed on them in a standard 12-lead format. A 12-lead trace was obtained using Sure-Grip alligator clips (available from 3M Company, St. Paul, Minn.) and a Mac 12 EKG machine (available from Marquette Electronics, Milwaukee, Wis.). Lift for each of the 10 leads was visually assessed before the leadwires were removed and grouped as follows: no lift, 1–10% lift, 11–25% lift, 26–50% lift, 51–75% lift, 76–99% lift, and 100% (electrode off). The commercially available Red Dot® Resting 2330 electrode (available from 3M Company, St. Paul, Minn.), which is the same dimensions but does not have a stripe of tackified Kraton adhesive adjacent to the tab, was run in similar fashion as a comparative example. As shown in Table I, the electrode with the stripe of Kraton had significantly lower lift scores.

TABLE 1

| LIFT VALUE - 120 TOTAL TESTS | | | | | | | |
|---|---|---|---|---|---|---|---|
| TYPE | NO LIFT | 1–10% | 11–25% | 26–50% | 51–75% | 76–99% | 100% |
| Example 1 | 109 | 11 | 0 | 0 | 0 | 0 | 0 |
| 2330 Electrode | 85 | 27 | 5 | 2 | 1 | 0 | 0 |

Percent "No Lift" for Example 1 Electrodes: 90.83%
Percent "No Lift" for 2330 Electrodes: 70.83%
Example 1 Electrodes were 20% better in resisting any lift over 120 tests.

If one were to assign a number to each set of lift percentages, 0 for No Lift; 1 for 1–10%; 2 for 11–25%; 3 for 26–50%; 4 for 51–75%; 5 for 76–99%; and 6 for Lift Off, then the average lift could then be estimated:
Average Lift for Example 1 Electrodes: 0.09
Average Lift for 2330 Electrodes: 0.39
Example 1 Electrodes were 23% better in resisting lift over 120 tests.

Stated either way, the electrodes of Example 1 have significantly better resistance to lift in a standard 12-lead trace environment of an ECG procedure.

EXAMPLE 2

Part A—Integrated Stripe Coating of Tackified Kraton Adhesive and Ionically Conductive Adhesive On a coating line with a forced air oven two die stations were set up between the film unwind and the oven. The first station held a heated 30.5 cm slot die having lips curved to the radius of a 11.4 cm diameter aluminum backup roll. The die was fitted with a 0.76 mm thick shim insert which was patterned with openings consisting of four pairs of stripes. Each pair was spaced 3.5 cm apart with 2.9 cm between the pairs. Each stripe was 0.5 cm wide. A Graco/LTI Dynamelt DM-5 pail unloader with heated platen and hose (both 175° C.) was used to deliver adhesive from a 19 liter pail to a Zenith pump which metered the adhesive to the die, also held at 175° C. The adhesive formulation was a mixture of 34.5 weight percent Kraton 1107® (a polystyrene-polyisoprene block copolymer available from Shell Chemical Co., Houston, Tex.), 52.5 weight percent Wingtack Plus® (a modified polyterpene tackifying resin available from Goodyear Tire and Rubber Co., Akron, Ohio), 11.0 weight percent Tufflo 6056® (a white mineral oil available from Lyondell Lubricants, Houston Tex.), and 2.0% Irganox® 1010 (an antioxidant available from Ciba-Geigy Corporation, Hawthorne, N.Y.). This higher rubber/higher triblock adhesive formulation was chosen to reduce the softening and flow that was experienced with the formulation described above. It was compounded using a twin screw extruder and placed in pails. The second die station held an unheated 30.5 cm slot fed extrusion die having lips curved to the radius of a 11.4 cm diameter aluminum backup roll. The second die was fitted with a 1.27 mm thick shim insert which was patterned with four 3.5 cm openings positioned 4.1 cm apart to allow for stripe coating of the ionically conductive adhesive precursor between the paired stripes of Kraton PSA. The conductive adhesive precursor was the same formulation as that described above and was delivered to the die in the same fashion. The same silver/silver chloride ink coated polyester substrate was unwound at 2 meters per minute past the two die stations. At the first station the tackified Kraton adhesive was coated to result in stripes 0.33 mm thick. The ionically conductive adhesive precursor was coated at the second station at 0.89 mm thick between the stripes of Kraton adhesive and dried by passing through the 18 meter long three zone oven with zone one set at 110° C., zone two at 130° C., and zone three at 120° C. The resulting film was wound up, laminating in an Akrosil siliconized polyethylene release liner. The dried conductive adhesive had a final thickness of 0.33 mm and a water content of 15 weight percent. Under these conditions the Kraton formulation used in this experiment did not flow during the drying process. A second run was conducted, keeping the material inputs and conditions the same but changing the shims in both dies. These new shims gave an additional 1.0 cm wide stripe of tackified Kraton adhesive centered between each of the four paired 0.5 cm wide stripes and blocked coating of the ionically conductive precursor from the area where this new Kraton stripe was being coated.

EXAMPLE 2

Part B—Converting to Electrodes and Testing

The 30.5 cm webs of adhesive were slit to four 7.6 cm wide webs with the coated 4.4 cm adhesive area centered in the middle and an uncoated 1.6 cm tab area on either side. This substrate was fed into a Mark Andy rotary converting machine, stripping the Akrosil liner, laminating to a 127 μm siliconized polyester product liner available from Daubert Coated Products, Westchester, Ill., kiss cutting electrodes out of the coated adhesive in the same format as described above, pulling a weed, and cutting out cards of electrodes using a sheeter die. Each card contains 10 electrodes with two across, five to a side, and tabs facing out. The adhesive coating described above with two 0.5 cm wide stripes of tackified Kraton PSA and a 3.5 cm stripe of conductive adhesive coated between them thus gives electrodes with a single stripe of tackified Kraton adhesive adjacent to the uncoated tab. The coating which further has a 1.0 cm stripe of Kraton centered in the middle gave on converting electrodes with 0.5 cm stripes of tackified Kraton adhesive both at the tab side and opposite. Both these electrodes were included in a resting EKG panel as described above except in this case Hirschmann alligator clips (available from 3M Company, St. Paul, Minn.) were used to connect the electrode tab to the instrument and an Electrotrace AG 1200+ electrode (available from Jason, Huntington Beach, Calif.) was used as the control. Lift scores for the 10 sites on twelve panelists were very low for all, averaging 0.04 for the Jason and the two stripe electrodes and 0.03 for the one stripe electrode.

The invention is not limited to the embodiments and examples described above. The present invention is hereby claimed with appreciation for equivalents of the invention.

What is claimed is:

1. A method of making an electrode, comprising:
   (a) providing a non-conductive flexible backing having a side having an electrically conductive surface;
   (b) coating at least one field of biocompatible pressure sensitive adhesive on the side wherein each field of biocompatible pressure sensitive adhesive contacts the electrically conductive surface; and
   (c) coating a field of conductive adhesive on the electrically conductive surface.

2. The method according to claim 1,
   wherein the electrically conductive surface of the flexible backing comprises a tab portion and a pad portion,
   wherein coating step (b) results in two separate opposing fields of biocompatible pressure sensitive adhesive contacting the side of the backing on the pad portion at locations proximal and distal to the tab portion, and
   wherein the coating step (c) results in conductive adhesive contacting the pad portion.

3. The method according to claim 2, wherein coating step (b) results in the two separate opposing fields of biocompatible pressure sensitive adhesive bisecting a line that also bisects the tab portion and the pad portion.

4. The method according to claim 1, wherein the coating step (c) results in conductive adhesive at a final thickness and the coating step (b) results in biocompatible pressure sensitive adhesive at a final thickness within 40 percent of the final thickness of the coated conductive adhesive.

5. The method according to claim 1, wherein the coating step (c) results in conductive adhesive at a final thickness and the coating step (b) results in biocompatible pressure sensitive adhesive at a final thickness within 20 percent of the final thickness of the coated conductive adhesive.

6. The method according to claim 1, wherein the coating step (c) results in conductive adhesive at a final thickness and the coating step (b) results in biocompatible pressure sensitive adhesive at a final thickness nearly equal to the final thickness of the coated conductive adhesive.

7. The method according to claim 1, wherein the coating step (b) coats one field of biocompatible pressure sensitive adhesive and wherein the method further comprises the step of (d) coating a second field of biocompatible pressure sensitive adhesive on the side.

8. A method of making an electrode, comprising:
   (a) providing a non-conductive flexible backing having a side having an electrically conductive surface;
   (b) coating at least one field of biocompatible pressure sensitive adhesive on the electrically conductive surface; and
   (c) coating a field of conductive adhesive on the electrically conductive surface;
   wherein all fields contacting the electrically conductive surface are coated to have similar final thickness.

9. The method of claim 8, wherein coating steps (b) and (c) result in no final thickness of any field contacting the electrically conductive surface disadvantages any other field in distance from contact with skin of a patient during use.

* * * * *